United States Patent [19]

Bentz et al.

[11] Patent Number: 5,393,739
[45] Date of Patent: Feb. 28, 1995

[54] USE OF BONE MORPHOGENETIC PROTEIN IN SYNERGISTIC COMBINATION WITH TGF-$\beta$ FOR BONE REPAIR

[75] Inventors: Hanne Bentz, Newark; Andrea Y. Thompson, Mountain View; Rosa Armstrong, Palo Alto; David M. Rosen, San Jose, all of Calif.

[73] Assignee: Celtrix Pharmaceuticals, Inc., Santa Clara, Calif.

[21] Appl. No.: 123,464

[22] Filed: Sep. 15, 1993

Related U.S. Application Data

[63] Continuation of Ser. No. 32,408, Mar. 15, 1993, abandoned, which is a continuation of Ser. No. 961,061, Oct. 14, 1992, abandoned, which is a continuation of Ser. No. 620,142, Nov. 30, 1990, abandoned.

[51] Int. Cl.$^6$ .................. C07G 7/00; A61K 37/02; A61K 35/32; A61K 37/12
[52] U.S. Cl. .............................. 514/12; 514/2; 514/21
[58] Field of Search .................. 514/2, 12, 21

[56] References Cited

U.S. PATENT DOCUMENTS

| 4,294,753 | 10/1981 | Urist | 530/840 X |
|---|---|---|---|
| 4,434,094 | 2/1984 | Seyedin et al. | 530/840 X |
| 4,455,256 | 6/1984 | Urist | 530/840 X |
| 4,563,489 | 1/1986 | Urist | 530/21 X |
| 4,608,199 | 8/1986 | Caplan et al. | 514/21 |
| 4,774,322 | 9/1988 | Seyedin et al. | 530/840 X |
| 4,789,732 | 12/1988 | Urist | 530/840 X |
| 4,795,804 | 1/1989 | Urist | 530/840 X |
| 4,806,523 | 2/1989 | Bentz et al. | 514/2 |
| 4,877,864 | 10/1989 | Wang et al. | 514/12 |
| 4,886,747 | 12/1989 | Derynk et al. | 435/69.4 |

FOREIGN PATENT DOCUMENTS

WO89/09787 10/1989 WIPO.
WO89/09788 10/1989 WIPO.

OTHER PUBLICATIONS

Bentz et al., "Cartilage Induction and Differentiation: The Role of Bone-Derived Cartilage Inducing Factor (CIF-A)", in Development and Diseases of Cartilage and Bone Matrix, pp. 137-147, 1987, Alan R. Liss, Inc.
Urist et al., "Surface-decalcified allogeneic bone (SDAB) implants", Clin. Orthop. & Rel. Res., (1968), 56:37-50.
Urist et al., "Bone: Formation by autoinduction", Science, (1965), 150:893-899.
Reddi et al., "Biochemical sequences in the transformation of normal fibroblasts in adolescent rats", Proc. Natl. Acad. Sci., (1972), 69:1601-1605.
Urist et al., "A bovine low molecular weight bone morphogenetic protein (BMP) fraction", Clin. Orthop. Rel. Res., (1982), 162:219-232.
Urist et al., "Bone cell differentiation and growth factors", Science, (1965), 150:893-899.
Urist et al., "Purification of bovine bone morphogenetic protein by hydroxyapatite chromatography", Proc. Natl. Acad. Sci., (1984), 81:371-375.
Wozney, J. M., "Bone morphogenetic proteins", Growth Factor Research, (1989), 1:267-280.
Ozkaynak et al., "OP-1 cDNA encodes an osteogenic proteins in the TGF-$\beta$ family", EMBO J., (1990), 9:2085-2093.
Sampath et al., "Bovine osteogenic protein is composed of dimers of OP-1 and BMP-2A, two members of the transforming growth factor-$\beta$ superfamily", J. Biol. Chem., (1990), 265:13198-13205.

(List continued on next page.)

Primary Examiner—Howard E. Schain
Assistant Examiner—P. Lynn Touzeau
Attorney, Agent, or Firm—Morrison & Foerster

[57] ABSTRACT

Bone morphogenetic proteins -2 and -3 (BMPs -2 and -3) work in synergistic combination with TGF-$\beta$z to provide compositions with increased osteogenic activity. Methods of treating bone defects, inducing bone growth and increasing bone marrow cell production using these compositions are also disclosed.

4 Claims, 5 Drawing Sheets

OTHER PUBLICATIONS

Jakowlew et al., "Complementary deoxyribonucleic acid cloning of a messenger ribonucleic acid encoding transforming growth factor β4 from chicken embryo chondrocytes", *Molec. Endocrinol.*, (1982), 2:1186–1195.

Roberts et al., "Isolation and characterization of TGF-β2 and TGF-β5 from medium conditioned by Xenopus XTC cells", *Growth Factors*, (1990), 2:135–147.

Bentz et al., "Purification and characterization of a unique osteroinductive factor from bovine bone", *J. Biol. Chem.*, (1989), 264(32):20805–20810.

Sen, A., et al., (eds.), *Development and Diseases of Cartilage and Bone Matrix*, Alan R. Liss, Inc., New York, (1987), pp. 137–147.

Kawamura et al., "Growth factors, mitogens, cytokines, and bone morphogenic protein in induced chondrogenesis in tissue culture", *Developmental Biology*, (1988), 130:435–442.

Reddi et al., "Bone induction by osteogenin and bone morphogenetic proteins", *Biomaterials*, (1990), 11:33–34.

Reddi et al., "Initiation of bone development by osteogenin and promotion by growth factors", *Connective Tissue Research*, (1989), 20:303–311.

Bentz et al., "Transforming growth factor-β2 enhances the osteoinductive activity of a bovine bone-derived fraction containing bone morphogenic protein-2 and 3", *Matrix*, (1991), 11:269–275.

Kukita et al., "Osteoinductive factor inhibits formation of human osteoclast-like cells", *Proc. Natl. Acad. Sci.*, (1990), 87:3023–3026.

Bonewald et al., "Role of transforming growth factor-beta in bone remodeling", *Clinical Orthopaedics and Related Research*, (1990), 250:261–276.

Centrella et al., "Transforming growth factor β is a bifunctional regulator of replication and collagen synthesis in osteoblast-enriched cell cultures from fetal rat bone", *J. Biol. Chem.*, (1987), 262(6):2869–2874.

Robey et al., "Osteoblasts synthesize and responsed to transforming growth factor-type β (TGF-β) in vitro", *J. Cell. Biol.*, (1987), 105:457–463.

Rosen et al., "Transforming growth factor-beta modulates the expression of osteoblast and chondroblast phenotypes in vitro", *J. Cell. Physiol.*, (1988), 134:337–346.

BMP-2, RESIDUES 295-396

SCKRHPLYVDFSDVGWNDWIVAPPGYHAFYCHGECPFPLADHLNSTNHAIV

L9: HPLYVDFSDVGLND—IVAP—
                           G

L10: —PLYVDFSDVGWNDWIVAP—GYHAFY—GE
       IVNSFQG
       YVTL

OTLVNSVNSKIPKACCVPTELSAISMLYLDENEKVVLKNYQDMVVEGCGCR

L6: A—NVPTELSAISMLYLDE    L2: NYQDMVVEG—GEN
      DPA                       DQP L   AN

BMP-3, RESIDUES 363-472

QWIEPRNCARRYLKVDFADIGWSEWIISPKSFDAYYCSGACQFPMPKSLKPSNHA

L3: —IEPRN—ATRYLK——DP—G—D    L4: SFDAY—SGA—QF—D
    PA  D EL F E    I

L8: VDFADIG—SE—ILSPKF—P    L5: PSNPA
             S  L V F   V  M            ALKVS

TIQSIVRAVGVVPGIPEPCCVPEKMSSLSILFFDENKNVVLKVYPNMTVESCACR

TIQSIVRAVGVVPGIPEP—E            L1: VYP—MTVES—A—R
NEATAQSIL  A  G    I                 QVALK ANV  E

L7: MS—LSILFFDENKL
             P DPPT   L

FIG. 4

USE OF BONE MORPHOGENETIC PROTEIN IN SYNERGISTIC COMBINATION WITH TGF-β FOR BONE REPAIR

This application is a continuation of application Ser. No. 08/032,408, filed Mar. 15, 1993, which is a CON of 07/961,061, filed Oct. 14, 1992, which is a CON of 07/620,142, filed Nov. 30, 1990, all now abandoned.

TECHNICAL FIELD

The present invention relates to osteoplasty. More particularly, it relates to a combination of proteins that induce bone growth, pharmaceutical compositions containing that combination, methods for promoting bone growth using such compositions, methods for stimulating bone marrow progenitor cells to divide and differentiate into bone marrow cells, and methods for treating diseases associated with dysfunction/malfunction of bone generation and/or bone resorption, such as osteoporosis.

BACKGROUND ART

It has been established that bone contains materials which can stimulate the formation of new bone when placed in contact with living systems. (Urist, M. R., *Clin Orthop* (1968) 56:37; *Science* (1965) 150:893; Reddi, A. H., et al., *Proc Natl Acad Sci (USA)* (1972) 69:1601.) Attempts have been made to purify whatever factors are responsible for this activity. A "bone morphogenetic protein" (BMP) was extracted from demineralized bone using urea or guanidine hydrochloride and reprecipitated according to the disclosures in U.S. Pat. Nos. 4,294,753 and 4,455,256 to Urist. Urist subsequently reported (Urist, M. R., *Clin Orthop Rel Res* (1982) 162:219) that ion exchange purification of this crude protein mixture yielded an activity which was unadsorbed to carboxymethyl cellulose resin (CMC) at pH 4.8. Urist's reports in *Science* (1983) 220:680–685 and *Proc Natl Acad Science* (USA) (1984) 81:371–375 describe BMPs having molecular weights of 17,500 and 18,500 daltons. Urist's patent publication, EPA Publication No. 0212474, describes BMP fragments of 4,000 to 7,000 daltons obtained by limited proteolysis of BMP.

U.S. Pat. No. 4,608,199 describes a bone-derived protein of 30,000–32,000 daltons. The protein is described as being water soluble and having no affinity for concanavalin A (ConA).

WO 88/00205 reports four proteins, designated BMP-1, BMP-2 Class I ("BMP-2"), BMP-3, and BMP-2 Class II ("BMP-4"), that are alleged to have osteogenic activity. It is not known whether these BMPs have osteogenic activity by themselves or require combination with other factors.

J. M. Wozney, in *Growth Factor Research*, Vol. 1 (1989), pp. 267–280, describes three additional BMP proteins closely related to BMP-2, and which have been designated BMP-5, BMP-6 and BMP-7.

WO 89/09787 and 89/09788 describe a protein called "OP-1" now known to be BMP-7. The cloning of BMP-7 is described in E. Ozkaynak et al., *EMBO Journal* (1990) 9:2085–2093, and the purification of BMP-7 is described in T. K. Sampath et al., *J Biol Chem* (1990) 265:13198–13205.

U.S. Pat. No. 4,434,094 to Seyedin and Thomas reported the partial purification of a bone generation-stimulating, bone-derived protein by extraction with chaotropic agents, fractionation on anion and cation exchange columns, and recovery of the activity from a fraction adsorbed to CMC at pH 4.8. This new protein fraction was termed "osteogenic factor" (OF) and was characterized as having a molecular weight below about 30,000 daltons.

Commonly owned U.S. Pat. No. 4,744,322 describes two bone-derived proteins that were purified to homogeneity by extraction with chaotropic agents, and ion exchange column fractionation. These two proteins were originally called cartilage-inducing factor (CIF) A and CIF B. CIF A was subsequently found to be identical to a previously identified protein called transforming growth factor beta (TGF-β). CIF B has been found to be a novel form of TGF-β and is now known as TGF-β2, while CIF A is known as TGF-β1.

Additional TGFs have also been described. U.S. Pat. No. 4,886,747 to Derynck et al., describes the identification of TGF-β3 and its nucleotide sequence, and describes a method for recovery of TGF-β3 from recombinant cell cultures. S. B. Jakowlew et al., *Molec Endocrinol* (1988) 2:1186–1195 describes TGF-β4 and its nucleotide sequence, identified by cDNA characterization. A. B. Roberts et al., *Growth Factors*, Vol. 2 (1990), pp. 135–147, describes the purification of TGF-β5 from Xenopus-conditioned medium.

A novel glycoprotein preparation from bovine bone designated osteoinductive factor (OIF), based on the ectopic osteoinductive activity used to follow its purification, has also been reported (Bentz, H., et al., *J. Biol. Chem.* (1989) 264:20805–20810). It was first thought that the osteoinductive activity of these "OIF preparations" could be substantially enhanced by either TGF-β1 or 2 (Bentz, H., et al., *J. Biol. Chem.* (1989) 264:20805–20810; Bentz, H., et al., *Development and Diseases Of Cartilage and Bone Matrix* (A. Sen and T. Thornhill eds.) pp. 137–147, Alan R. Liss, Inc. (1987) New York). However, it was later found that the factors believed to have OIF activity did not in fact have that activity.

It is not known whether bone-inducing activity in isolated preparations is attributable to a single protein or a plurality of proteins acting in concert. Identification of the protein(s) responsible for bone-inducing activity is complicated by the large number of proteins extracted from bone (estimated to be several hundred), and the lack of a conclusive in vitro assay for bone-inducing activity.

SUMMARY OF THE INVENTION

The invention results from two unpredicted discoveries. The first is that the bone generation-stimulating activity in the partially purified "OIF preparation" from bovine bone is apparently due to the presence of BMPs in the preparation, including BMP-2, BMP-3, BMP-4 and BMP-7. The second is that the TGF-βs have a cell-proliferative effect such that when co-administered with the BMPs, including BMP-2, BMP-3, BMP-4 and BMP-7, a synergistic effect in osteogenic activity is obtained.

Accordingly, it is a primary object of this invention to provide a composition for treating cartilage and/or bone defects containing a BMP and a TGF-β.

It is a further object of this invention to provide a method of treating bone defects in vivo at a predetermined site in a living mammal.

It is another object of this invention to provide a method of inducing bone marrow cell production in a living mammal.

Additional objects, advantages and novel features of the invention will be set forth in part in the description which follows, and in part will become apparent to those skilled in the art upon examination of the following, or may be learned by practice of the invention.

In one aspect of the invention, a composition for treating cartilage and/or bone defects in vivo is provided comprising (a) an effective tissue-growth-inducing amount of a bone morphogenetic protein (BMP) and a transforming growth factor beta (TGF-$\beta$) combined with (b) a pharmaceutically acceptable carrier.

In another aspect of the invention, a method of treating cartilage and/or bone defects in vivo at a desired site is provided, comprising implanting the above described composition in a mammal at said site.

In yet another aspect of the invention, a method of inducing bone marrow cell production in a living mammal is provided, comprising administering an effective tissue-growth inducing amount of the above-described composition systemically to the mammal.

BRIEF DESCRIPTION OF THE FIGURES

FIG. 4 compares peptide sequences of peak 1 proteins with BMP-2 and BMP-3 sequences.

DETAILED DESCRIPTION OF THE INVENTION

Definitions

Figure 1:
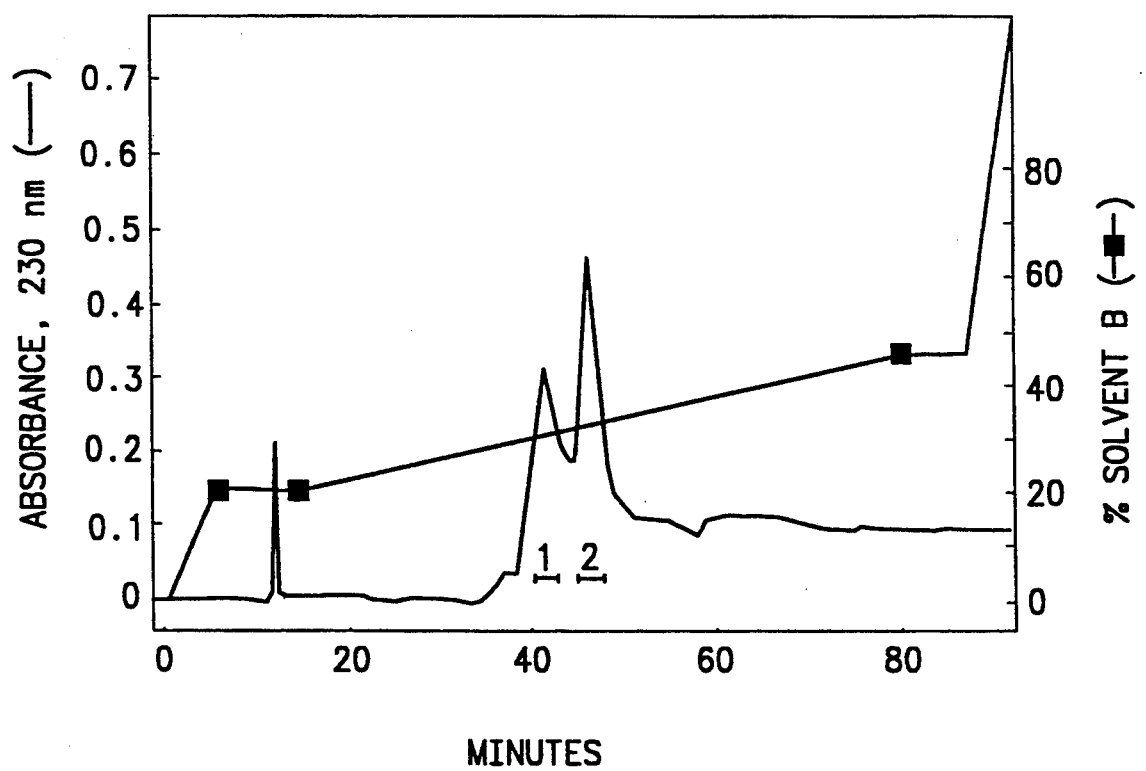
FIG. 1 shows the RP-HPLC chromatographic fractionation of an osteoinductive factor-containing fraction.

As used herein, "bone morphogenetic protein" (BMP) refers to a class of bone-derived proteins capable of inducing bone formation, as measured by activity in an in vivo rat bone formation assay. BMPs include BMP-1, BMP-2, BMP-3, BMP-4, BMP-5, BMP-6 and BMP-7, and fragments, deletions, additions, substitutions, mutations and modifications thereof which retain the biological characteristics of the natural BMP. The BMP may be of human, bovine, or other species origin.

As used herein, "transforming growth factor beta" (TGF-$\beta$) refers to a family of polypeptides capable of inducing cell proliferation including TGF-$\beta$1, TGF-$\beta$2, TGF-$\beta$3, TGF-$\beta$4, and TGF-$\beta$5, and to fragments, deletions, additions, substitutions, mutations and modifications thereof which retain the biological characteristics of the naturally occurring TGF-$\beta$. The TGF-$\beta$ may be of human, bovine, or other species origin.

A "mutation" in a protein alters its primary structure (relative to the commonly occurring protein) due to changes in the nucleotide sequence of the DNA which encodes it. These mutations include genetically engineered variants as well as allelic variants. A "modified" protein differs from the commonly occurring protein as a result of post-translational events which change the glycosylation or lipidation pattern, or the primary, secondary, or tertiary structure of the protein. Changes in the primary structure of a protein can also result from deletions, additions or substitutions. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral polar, or neutral nonpolar. Furthermore, three of the naturally-occurring amino acids are aromatic. It is generally preferred that encoded peptides differing from the natural BMPs and TGF-$\beta$s contain substituted codons for amino acids which are from the same group as that of the amino acid replaced. Thus, in general, the basic amino acids Lys, Arg, and His are interchangeable; the acidic amino acids aspartic acid and glutamic acid are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Thr are interchangeable. While proline is a nonpolar neutral amino acid, it creates difficulties because of its effects on conformation, and substitutions by or for proline are not preferred, except when the same or similar conformational results can be obtained. Polar amino acids which represent conservative changes include Ser, Thr, Gln, Asn; and, to a lesser extent, Met. In addition, although classified in different categories, Ala, Gly, and Ser seem to be interchangeable, and Cys additionally fits into this group, and may be alternatively classified with the polar neutral amino acids.

It should further be noted that if either the BMP or the TGF-$\beta$ or both is made synthetically, substitutions by amino acids which are not encoded by a naturally-occurring gene may also be made. Alternative residues include, for example, the $\omega$-amino acids of the formula $H_2N(CH_2)_nCOOH$ wherein n is 2–6. These are neutral, nonpolar amino acids, as are sarcosine, t-butyl alanine, t-butyl glycine, N-methyl-isoleucine, and norleucine. Other amino acids such as phenylglycine, for example, can be substituted for Trp, Tyr or Phe as an aromatic neutral amino acid; citrulline and methionine sulfoxide are neutral polar, cyclohexyl alanine is neutral nonpolar, cysteic acid is acidic, and ornithine is basic. The conformation-conferring properties of substituted proline residues may be retained if one or more of these is substituted with hydroxyproline.

The biological "characteristics" of a protein refer to the structural or biochemical function of the protein in the normal biological processes of the organism in which the protein naturally occurs. Examples of biological characteristics of a BMP include its specific antigenicity or immunogenicity, and/or its bone-inducing activity. Biological characteristics of a TGF-$\beta$ include its specific antigenicity or immunogenicity, and/or its ability to mediate inflammatory and chemotactic responses in vivo.

The term "effective amount" as used herein intends that quantity of a therapeutic agent that, when administered to a patient, is required to provide the desired or intended beneficial effect without intolerable side effects, such as toxicity.

The Composition

There are two active components in the compositions of this invention: a BMP protein and a TGF-$\beta$ protein. Together, these components work synergistically with respect to the osteogenic properties of the composition.

Preferably, the BMP component includes BMP-2, BMP-3, BMP-4, BMP-7 or mixtures thereof. Most preferably, the BMP component is a mixture of BMP-2 and BMP-3. Preferably, the TGF-$\beta$ component includes TGF-$\beta$1 or TGF-$\beta$2 or both, most preferably TGF-$\beta$2.

Both components may be prepared in one of three ways: (1) preparative methods of isolation and purification of the naturally occurring product; (2) synthetic methods; and (3) recombinant methods.

Preparative Methods

Isolation and purification of BMP-1, BMP-2, BMP-3 and BMP-4 is described in U.S. Pat. No. 4,877,864, the disclosure of which is incorporated herein by reference. The isolation and purification of BMP-7 is described in T. K. Sampath et al., *J Biol Chem* (1990) 265:13198–13205.

Isolation and purification of TGF-$\beta$1 and TGF-$\beta$2 is described in U.S. Pat. No. 4,774,332, the disclosure of which is incorporated herein by reference. The isolation and purification of TGF-$\beta$5 is described in A. B. Roberts et al., *Growth Factors*, Vol. 2 (1990), pp. 135–147.

Synthetic Methods

The BMPs and TGF-$\beta$s of the present invention can be synthesized chemically by means well known in the art such as, e.g., solid-phase peptide synthesis. Their amino acid sequences are known or deduced from their art-known nucleotide sequences. The synthesis is commenced from the carboxy-terminal end of the peptide using an $\alpha$-amino protected amino acid. t-Butyloxycarbonyl (Boc) protective groups can be used for all amino groups even though other protective groups are suitable. For example, Boc-Lys-OH or Boc-Arg-OH (i.e., BMP-like carboxy-terminal amino acids) can be esterified to chloromethylated polystyrene resin supports. The polystyrene resin support is preferably a copolymer of styrene with about 0.5 to 2% divinyl benzene as a cross-linking agent which causes the polystyrene polymer to be completely insoluble in certain organic solvents. See Stewart, et al., *Solid-Phase Peptide Synthesis* (1969), W. H. Freeman Co., San Francisco, and Merrifield, *J. Am. Chem. Soc.* (1963) 85:2149–2154. These and other methods of peptide synthesis are also exemplified by U.S. Pat. Nos. 3,862,925; 3,842,067; 3,972,859; and 4,105,602.

The synthesis may use manual techniques or automatically employing, for example, an Applied Biosystems 430A Peptide Synthesizer (Foster City, Calif.) or Biosearch SAM II automatic peptide synthesizer (Biosearch, Inc., San Rafael, Calif.), following the instructions provided in the instruction manual supplied by the manufacturer.

Of course, since automated synthesis also permits control of the sequence, additions, substitutions and deletions in the amino acid sequence are available using this method of synthesis. In addition, it is not necessary that a substituted amino acid be encoded by a gene. Therefore, the D-forms or $\beta$- or $\omega$-amino acids can be substituted for those natively present.

Recombinant Methods.

The BMPs and TGF-$\beta$s of the present invention may also be made, using their identified and isolated nucleotide sequences, and using conventional techniques of molecular biology, microbiology, recombinant DNA, and immunology, which are within the skill of the art. Such techniques are explained fully in the literature. See, e.g., Maniatis, Fritsch and Sambrook, *Molecular Cloning: A Laboratory Manual* (1982); *DNA Cloning,* Volumes I and II (D. N. Glover ed. 1985); *Oligonucleotide Synthesis* (M. J. Gait ed. 1984); *Nucleic Acid Hybridization* (B. D. Hames and S. J. Higgins eds. 1984); *Transcription and Translation* (B. D. Hames and S. J. Higgins eds. 1984); *Animal Cell Culture* (R. K. Freshney ed. 1986); *Immobilized Cells and Enzymes* (IRL press, 1986); Perbal, B., *A Practical Guide to Molecular Cloning* (1984); *Gene Transfer Vectors for Mammalian Cells* (J. H. Miller and M. P. Calos eds, Cold Spring Harbor Laboratory, 1987); the series, *Methods in Enzymology* (S. Colowick and N. Kaplan eds., Academic Press, Inc.), and *Handbook of Experimental Immunology,* Volumes I–IV (D. M. Weir and C. C. Blackwell eds., 1986, Blackwell Scientific Publications).

Recombinantly produced modified forms of a BMP or TGF-$\beta$ may be obtained by mutagenesis of a sequence encoding a BMP or TGF-$\beta$, for example, by site directed mutagenesis, as well as by deletions or insertions of sequences. Techniques for causing mutations are known to those of skill in the art. See, for example, Maniatis et al., supra., Perbal, B., supra., *Methods in Enzymology,* supra., and *Gene Transfer vectors for Mammalian Cells,* supra.

The foregoing methods to obtain the BMP and TGF-$\beta$ polypeptides of the invention are not intended to be limiting, and those components of the invention may be prepared in any convenient manner.

In view of the showing that bone-inductive proteins from human, monkey, bovine and rat sources are nonspecies-specific in their ability to produce endochondral bone in xenogeneic implants (Sampath, T. K., et al., *Proc Natl Acad Sci* (USA) (1983) 80:6591) it is believed that the BMPs and TGF-$\beta$s described herein are highly conserved among mammalian species—i.e., corresponding bone-inducing proteins from different mammalian species (herein called "species analogs") will have substantially homologous amino acid sequences that vary from, e.g., the bovine protein, if at all, in one or more amino acid residue additions, deletions or substitutions and/or substantially similar glycosylation patterns that do not affect the nonspecies-specific ability of the molecule to induce bone formation. In this regard, the terms "substantially equivalent" and "substantially homologous" are intended to mean proteins, regardless of species or method of preparation, that have the same amino acid sequence as the bovine osteogenic proteins described in the examples and proteins of similar but different amino acid sequence, which difference(s) does not affect nonspecies-specific endochondral bone-inducing activity adversely. The amino acid sequences of such "substantially homologous" proteins will usually be at least 50% homologous, more usually at least 80% homologous, and preferably at least 90% homologous to the bovine proteins described herein. Accordingly, such proteins may be derived from bone of diverse mammalian origin or synthesized using recombinant DNA procedures.

The BMP and TGF-β proteins of the invention, depending on the pH of their environment if suspended or in solution, or of their environment when crystallized or precipitated if in solid form, may be in the form of pharmaceutically acceptable salts or may be in neutral form. The free amino groups of the proteins are capable of forming acid addition salts with, for example, inorganic acids such as hydrochloric, phosphoric, or sulfuric acid; or with organic acids such as, for example, acetic, glycolic, succinic, or mandelic acid. The free carboxyl groups are capable of forming salts with bases, including inorganic bases such as sodium, potassium, or calcium hydroxides, and such organic bases such as piperidine, glucosamine, trimethylamine, choline, and caffeine. In addition, the proteins may be modified by combination with other biological materials such as lipids and saccharides, or by side chain modification such as acetylation of amino groups, phosphorylation or hydroxyl side chains, or oxidation of sulfhydryl groups. All of these-modifications are included within the scope of the definition.

Modes of Administration

The osteogenic compositions of the invention may be used to induce de novo bone formation in circumstances where bone is not normally formed. The composition may thus also be used to treat a variety of bone defects: it may be used prophylactically to reduce the likelihood of fracture, to improve fixation of artificial joints, to repair congenital or trauma-induced bone defects, or in cosmetic plastic surgery. The composition may also be used to enhance bone formation in instances where bone is normally formed, such as in fracture repair, replacement of surgically removed bone, or repair of bone damaged by periodontal disease or in other tooth or alveolar ridge repair processes. In such uses, the composition will be administered locally, such as by implantation, at the desired site of bone formation.

The composition may also be administered systemically, such as intravenously, to treat indications associated with insufficient bone formation and/or undesirable levels of bone resorption such as localized, regionalized or generalized osteoporosis or to stimulate bone marrow progenitor cells in the treatment of malfunctions or dysfunctions of the hematopoietic system such as chronic and acute mylocytic leukemia and other cancers of the hematopoietic system or in post-irradiation treatment to stimulate bone marrow stem cells to divide and differentiate.

The osteogenic composition of the invention will normally be formulated in osteogenically effective amounts with pharmaceutically acceptable solid or fluid carriers, for local injection or implantation at the desired site of activity or systemic administration by conventional parenteral routes. Preferably the formulations for local administration include a matrix material that is capable of presenting the protein at the desired site of activity as well as providing a structure for developing bone and cartilage. Potential matrices may be biodegradable or nonbiodegradable and be chemically or biologically defined. Examples of such materials are calcium sulfate, hydroxyapatite, tricalciumphosphate, polyorthoesters, polylactic- polyglycolic acid copolymers, collagen, bioglass, and the like. Formulations for systemic administration will typically involve liquid vehicles that are commonly used for parenteral administration of proteinaceous therapeutics.

The osteogenic composition of the invention may be conjugated with other molecules to increase its water-solubility, increase its half-life, or enhance its ability to bind to bone. For instance, the proteins may be conjugated to polyethylene glycol to increase their water solubility or to bone-binding molecules such as bisphosphonates (e.g. 1-hydroxyethylidene-1,1-bisphosphonic acid, dichloromethylene bisphosphonic acid, and 3-amino-1-hydroxypropylidene-1,1-bisphosphonic acid) and fluorochromes (e.g. tetracyclines, calcein blue, xylenol orange, calcein green, and alizarin complexone red) to target the proteins to bony sites. Various agents for conjugating molecules to proteins are well known in the art and include aldehydes, carbodiimides, and other bifunctional moieties.

The amount of the osteogenic composition administered may vary depending upon the carrier used, the patient (age, sex, medical history, species) and the site and condition being treated. For local implantation, the weight ratio of both BMP and TGF-β to carrier in the formulation will typically be in the range of about 1:5,000 to 1:50,000. The weight ratio of BMP to TGF-β in the composition will usually be in the range of 10:1 to 1:10. The implant may be placed at a predetermined site in the patient by conventional surgical techniques, such as implantation or injection.

For systemic administration the amount of total BMP and TGF-β will usually range between 20 μg/kg body weight and 2 mg/kg body weight. In addition it may be desirable to combine the BMP and TGF-β proteins with other therapeutics, such as, in the case of osteoporosis, fluoride, calcitonin, vitamin D metabolites, and parathyroid hormone. Because the composition is nonspecies-specific in its activity it may be used to treat mammals in general including sport, pet, farm animals and humans.

The following example is intended to illustrate but not limit the invention.

EXAMPLE

A. Purification of BMPs from an OIF Preparation

OIF preparations were obtained from a 4M guanidine-HCl extract of demineralized bovine bone by sequential application of five chromatographic steps, the last consisting of RP-HPLC using an acetonitrile gradient (see Bentz, H., et al., *J. Biol. Chem.* (1989) 2.64:20805–20810).

For further purification of the OIF preparations, fractions containing the bulk of the OIF were pooled, diluted with two volumes of 0.1% TFA, and rechromatographed on the same column using an n-propanol gradient. Solvent A was 0.1% TFA and solvent B was 90% n-propanol in solvent A. Proteins were eluted from the column with a linear gradient of 20–45% solvent B in solvent A at 0.4%/min and a flow rate of 1.2 ml/min.

Two major peaks were obtained as shown in FIG. 1. Protein concentration was determined by the BCA Pierce assay (Smith, P. K., et al., *Anal. Biochem.* (1985) 150:76–8613), and by comparing peak area (absorbance at 230 nm) with the peak area of a standard sample of bovine serum albumin. Proteins were analyzed by electrophoresis on 15% polyacrylamide gels by the method of U. K. Laemmli (*Nature* (1970) 227:680–685), as modified by F. W. Studier (*J. Mol. Biol.* (1973) 79:237–248). Gels were stained with silver and western blot analysis was performed using a monoclonal antibody specific for OIF (Dasch, J. R., et al., *J. Bone Min. Res.* (1989) 4:S286 (abstr.)).

The later eluted peak (Peak 2) contained OIF as characterized by its gel electrophoretic properties and immunochemical staining (Bentz, H., et al., *J. Biol. Chem.* (1989) 264:20805-20810). Peak 1 represented 10-40% of total protein in various samples as measured by peak area.

Figure 2:
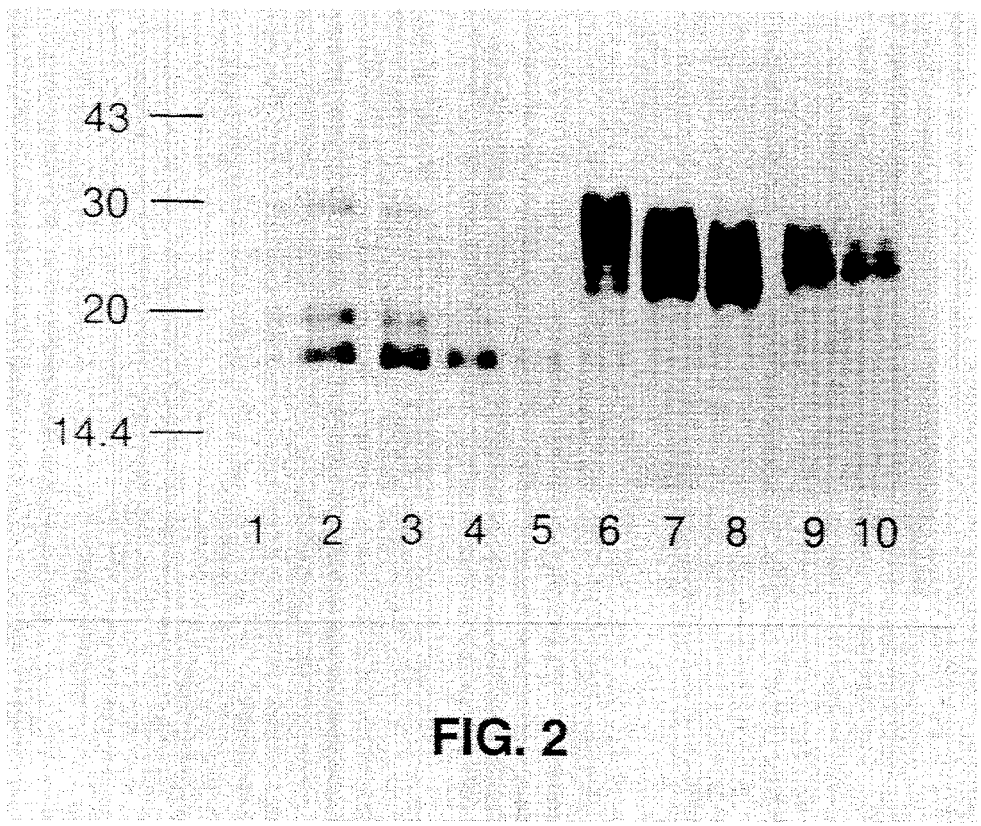
FIG. 2 shows the results of SDS-PAGE on several fractions obtained in the process of FIG. 1.

When fractions 40-49 in FIG. 1 were analyzed by SDS-PAGE (lanes 1-10 shown in FIG. 2), peak 1 material (lanes 2-4) was found to contain several components migrating in the mass range of 28-34 kDa, which on reduction were converted to components of 30, 18 and 16 kDa in relative amounts of 1, 3 and 4, respectively. This behavior is characteristic of BMP preparations as reported by Wang et al. (*Proc. Natl. Acad. Sci USA* (1988) 85:9484-9488) and Luyten et al. (*J. Biol. Chem.* (1989) 264:13377-13380).

Figure 3:
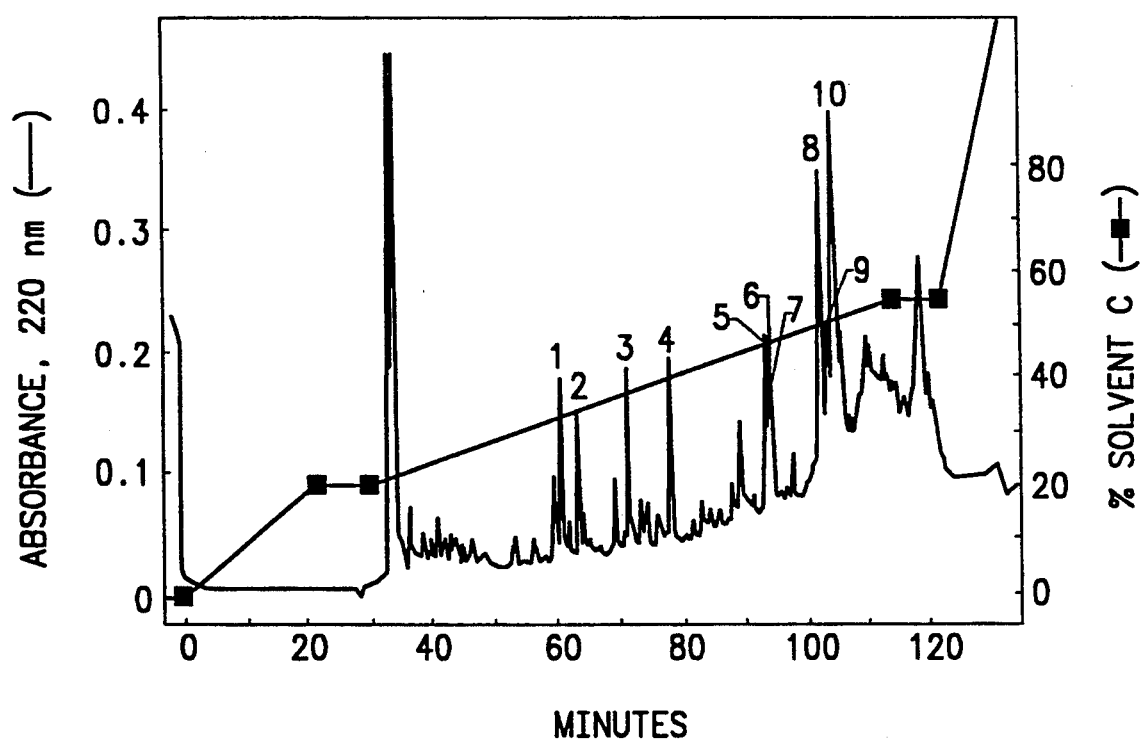
FIG. 3 shows the RP-HPLC fractionation of material from the first peak of FIG. 1.

To confirm this identification and determine the BMP species, peak 1 proteins were subjected to peptide analysis. Reduction, S-pyridylethylation, cleavage with endoproteinase Lys-C (Boehringer Mannheim), and peptide purification were performed essentially as described in H. Bentz et al., *J. Biol. Chem.* (1990) 265:5024-5029. The peptide mixture resulting from the proteolytic cleavage of peak 1 proteins was fractionated by RP-HPLC on a Vydak C18 column, 2.1×150 mm (FIG. 3). Solvent A was 0.1% TFA and solvent C was 90% acetonitrile in solvent A. The column was eluted with a linear gradient of 0-20% solvent C in solvent A at 1%/min followed by a 20-54% linear gradient of the same solvents at 0.4%/min and a flow rate of 0.25 ml/min.

Selected fractions from this separation were then sequenced. Peptides were sequenced by automated Edman degradation on a model 475A microprotein sequencer (Applied Biosystems) equipped with a model 120A on-line microbore phenylthiohydantoin derivative analyzer (Applied Biosystems). The sequences (L1 through L10, shown in FIG. 4) were compared to the known sequences of BMP-1-4 (Wozney, J. M., et al., *Science* (1988) 242:1528-1534; Wozney, J. M., et al., *Prog. Growth Factor Res.* (1990) 1:267-280). Although the peptides were not pure, as shown by secondary residue assignments at some sites and some residues that did not match, it is apparent that the peptides could only have come from a mixture of BMP-2 and BMP-3.

B. Osteoinductive Activity of Peak 1 Proteins and the Synergistic Effect of TGF-βs.

The osteoinductive activity of BMP-2 and BMP-3 (together "BMP-2+3"), as represented by peak 1 material, and of OIF, as represented by peak 2 material, was measured in the following rat subcutis model.

Peak 1 or 2 material was mixed with a carrier of porous particulate hydroxyapatite/tricalcium phosphate (Zimmer, Warsaw, Ind.) and bovine dermal collagen (Vitrogen, Collagen Corporation), lyophilized, hydrated with phosphate-buffered saline, and compacted into pellets weighing about 50 mg each (dry weight). The pellets contained 120 ng peak 1 or 2 material per mg. Some pellets also contained 140 ng TGF-β2 per mg. Pellets, usually four per group, were implanted into the subcutaneous tissue of 34- to 40-day-old male Sprague-Dawley rats as previously described (Bentz, H., et al., *J. Biol. Chem.* (1989) 264:20805-20810). After 14 days, pellets were explanted and evaluated for mineralization by assaying for alkaline phosphatase activity and for bone and cartilage by histological methods as previously described (Bentz, H., et al., *J. Biol. Chem.* (1989) 264:20805-20810). TGF-β1 and 2 were isolated from bovine bone as previously described (Seyedin, S. M., et al., *Proc. Natl. Acad. Sci. USA* (1985) 82:2267-2271; Seyedin, S. M., et al., *J. Biol. Chem.* (1986) 261:5693-5695; Seyedin, S. M., et al., *J. Biol. Chem.* (1987) 262:1946-1949).

As shown in Table 1, at 14 days BMP-2+3 (peak 1 material) induced extensive bone formation and increased alkaline phosphatase activity both with and without TGF-β2 in this experiment. Cartilage induction by BMP-2+3, on the other hand, was markedly stimulated by TGF-β2. OIF (peak 2 material) without TGF-β2 was completely inactive. With TGF-β2, OIF explants occasionally showed both cartilage and bone as illustrated in Table 1. This finding suggests that some BMP contamination remained in some OIF samples. OIF added to BMP-2+3 had no effect with or without TGF-β2.

TABLE

| In vivo osteoinductive activity of BMP-2+3 and OIF | | | |
|---|---|---|---|
| Material | Cartilage Hist.[a] | Bone Hist.[a] | ALPase[b] |
| −TGF-β2 | | | |
| BMP-2+3 | trace | 4.0 | 15.4 |
| OIF | 0 | 0 | 2.3 |
| BMP-2+3/OIF | trace | 3.25 | 11.8 |
| +TGF-β2 | | | |
| BMP-2+3 | 3.25 | 4.5 | 12.5 |
| OIF | 0.75[c] | 0.75[c] | 4.6[c] |
| BMP-2+3/OIF | 3.0 | 4.75 | 10.7 |

[a]evaluated on a scale of 0-5 (highest)
[b]expressed as μmoles p-nitrophenol/min/g wet weight
[c]represents activity in one of four samples.

Figure 5A:
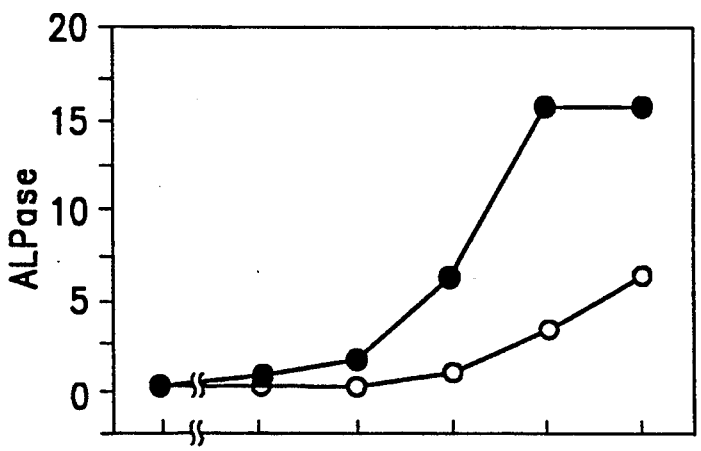
FIG. 5 show the bone-inductive properties of BMP-2+3 implants with TGF-$\beta$ (●) and without TGF-$\beta$ (○). Implants were assayed for alkaline phosphatase (ALPase) activity, and evaluated histologically for bone (B) and cartilage (C) on a scale of 0–5 (highest).
Figure 5B:
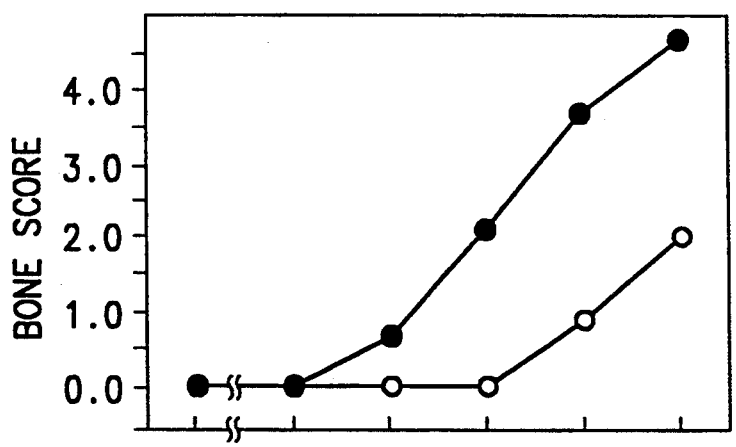
Figure 5C:
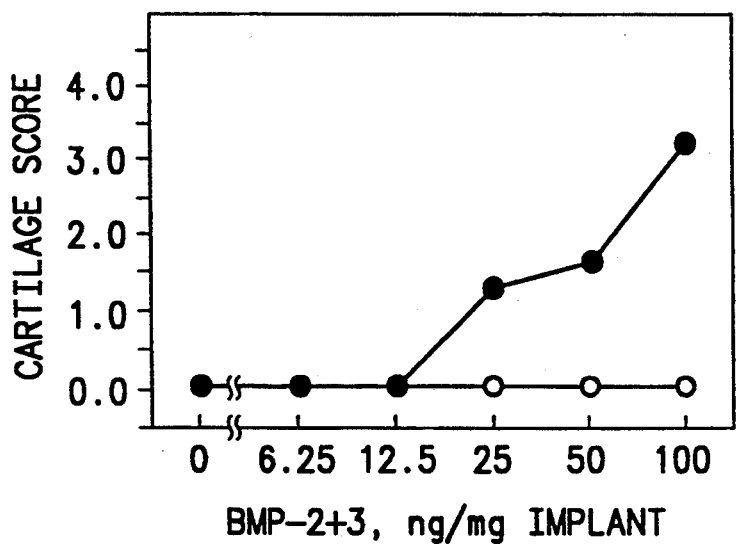

To more adequately show the effect of TGF-β2 on modulation of the osteoinductive activity of BMP-2+3, BMP-2+3 dose-response curves with and without TGF-β2 were determined again at 14 days. As shown in FIG. 5, the effect of TGF-β2 in potentiating both cartilage and bone formation is clearly evident. Without TGF-β2, BMP-2+3 was essentially inactive at levels up to 25 ng/mg implant and cartilage was absent at all levels. With TGF-β2, potentiation was evident at levels of BMP-2+3 at and above 12.5 ng/mg implant and cartilage was present at and above 25 ng/mg implant.

The data at this single time point in endochondral bone formation induced by BMP-2+3, represented by the two experiments described here, strongly suggest that TGF-β2 increases early cartilage formation and delays the onset of cartilage degeneration and replacement by bone. TGF-β1 in other experiments gave similar results.

What is claimed is:

1. A composition for treating cartilage and/or bone defects consisting essentially of:
   bone morphogenetic protein-2 (BMP-2), bone morphogenetic protein-3 (BMP-3), transforming growth factor-β2 (TGF-β2) together in a tissue-growth-inducing amount; and a pharmaceutically acceptable carrier or excipient.

2. An osteogenic composition for inducing bone growth consisting essentially of:
   bone morphogenetic protein-2 (BMP-2), bone morphogenetic protein-3 (BMP-3), and transforming growth factor-β2 (TGF-β2) together in a bone-growth-inducing amount; and a pharmaceutically acceptable carrier or excipient.

3. A method for treating bone and cartilage formation in an individual having a cartilage or bone defect comprising:

administering to the individual a composition consisting essentially of bone morphogenetic protein-2 (BMP-2), bone morphogenetic protein-3 (BMP-3) and transforming growth factor-$\beta2$ (TGF-$\beta2$) together in a tissue-growth-inducing amount, and a pharmaceutically acceptable carrier or excipient.

4. A method for inducing bone marrow cell production in an individual comprising:

administering to the individual a composition consisting essentially of bone morphogenetic protein-2 (BMP-2), bone morphogenetic protein-3 (BMP-3) and transforming growth factor-$\beta2$ (TGF-$\beta2$) together in a bone marrow cell growth-inducing amount, and a pharmaceutically acceptable carrier or excipient.

* * * * *